United States Patent [19]

Suzuki et al.

[11] Patent Number: 5,532,380

[45] Date of Patent: Jul. 2, 1996

[54] R,R,S,S-2-NITROIMIDAZOLE DERIVATIVES

[75] Inventors: Toshimitsu Suzuki; Azuma Nishio, both of Yokohama, Japan

[73] Assignee: Pola Chemical Industries, Inc., Shizuoka, Japan

[21] Appl. No.: 256,354

[22] PCT Filed: Oct. 21, 1993

[86] PCT No.: PCT/JP93/01519

§ 371 Date: Jul. 18, 1994

§ 102(e) Date: Jul. 18, 1994

[87] PCT Pub. No.: WO94/14778

PCT Pub. Date: Jul. 7, 1994

[30] Foreign Application Priority Data

Dec. 18, 1992 [JP] Japan ..................... 4-339035
Feb. 3, 1993 [JP] Japan ..................... 5-016530

[51] Int. Cl.$^6$ .............. C07D 233/91; C07D 233/94; C07C 69/63; C07C 69/76; A61K 31/415
[52] U.S. Cl. ......................... 548/327.5; 560/264
[58] Field of Search ............ 548/327.5; 560/264; 514/398

[56] References Cited

U.S. PATENT DOCUMENTS

| | | | |
|---|---|---|---|
| 2,314,454 | 3/1943 | Manchen et al. | 560/264 X |
| 2,377,878 | 6/1945 | Gresham | 560/264 X |
| 2,901,506 | 8/1959 | Bullock et al. | 560/264 X |
| 3,468,902 | 9/1969 | Beaman et al. | 548/327.5 |
| 4,456,610 | 6/1984 | Hofheinz et al. | 548/327.5 X |
| 4,462,992 | 7/1984 | Agrawal et al. | 548/327.5 X |
| 4,945,102 | 7/1990 | Suzuki et al. | 514/398 |
| 5,270,330 | 12/1993 | Suzuki et al. | 514/398 |

FOREIGN PATENT DOCUMENTS

| | | | |
|---|---|---|---|
| 0753930 | 12/1970 | Belgium | 560/264 |
| 0513351 | 11/1992 | European Pat. Off. | 548/327.5 |
| 58-170725 | 10/1983 | Japan | 560/264 |
| 59-139363 | 8/1984 | Japan | 548/327.5 |
| 62-283943 | 12/1987 | Japan | 560/264 |
| 63-30491 | 2/1988 | Japan | 560/264 |
| 3-223358 | 10/1991 | Japan | 548/327.5 |
| 0999909 | 7/1965 | United Kingdom | 560/264 |

OTHER PUBLICATIONS

Hakimelahi et al, Chemical Abstracts, vol. 107, #237190C (1987).
Smirnov et al, Chemical Abstracts, vol. 114, #82391n (1991).
Al–Hakim et al., Synthesis, Feb. 1985, pp. 207–208.
Ohno et al., Chem. Pharm. Bull., 1985, 33(2), 572–582.
Hakimelahi et al., Helvetica Chimica ACTA, 1987, 70, 219–231.
Takano et al., Synthesis, 1986, (10), 811–817.

*Primary Examiner*—Floyd D. Higel
*Attorney, Agent, or Firm*—Bacon & Thomas

[57] ABSTRACT

High purity 2-nitroimidazole derivatives having excellent radiosensitivity and high safety and useful as a drug to be used along with radiotherapy of various cancers can be prepared at a high yield from inexpensive diester of tartaric acid according to the following reaction formua,

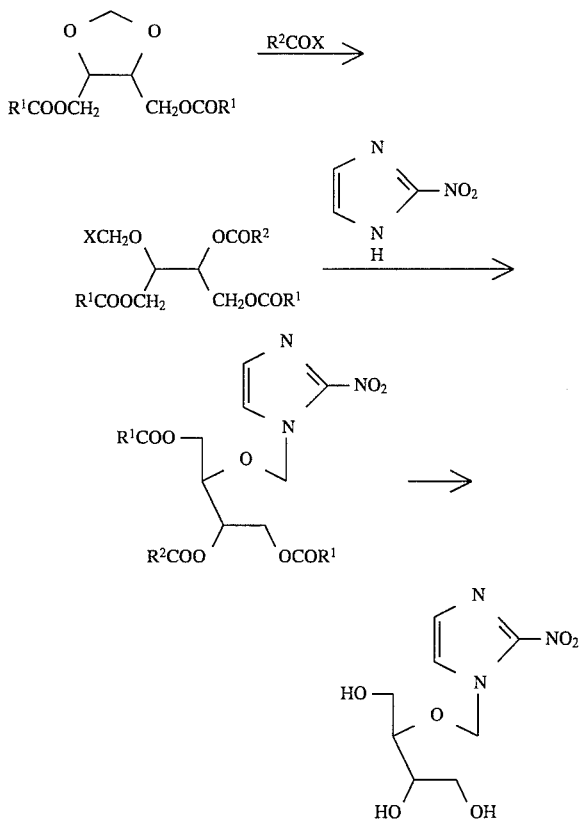

wherein $R^1$ and $R^2$ may be the same or different and each individually represents an aliphatic group or an aromatic group, and X represents a halogen atom.

9 Claims, No Drawings

R,R,S,S-2-NITROIMIDAZOLE DERIVATIVES

This application is a 371 of PCT/JP 93/01519 filed Oct. 20, 1993.

FIELD OF TECHNOLOGY

The present invention relates to an optically active 2-nitroimidazole derivative which is useful as a drug used along with radiotherapy of cancers, a radiosensitizer comprising the same as an effective component, a process for preparing the same, and an intermediate for the preparation of this derivative.

BACKGROUND ART

A 2-nitroimidazole derivative represented by the following formula (5) exhibits an action of promoting radiosensitivity of hypoxic cells existing in cancers. Because it has the excellent radiosensitivity and is highly safe, this compound is known to be useful as a drug used along with radiotherapy of cancer (Japanese Patent Application Laid-open (kokai) No. 223258/1991).

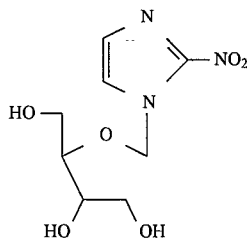

(5)

A process of the following reaction scheme is known for preparing the 2-nitroimidazole derivative (5).

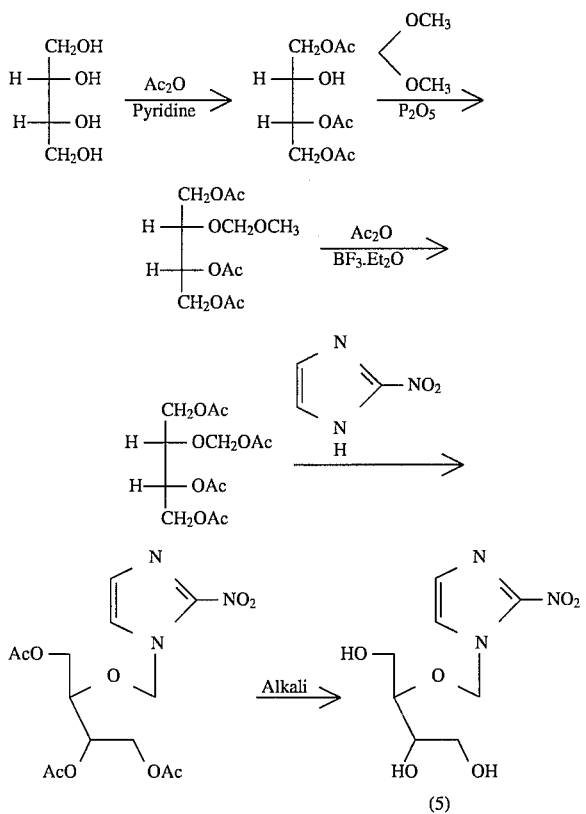

This process comprises a step of selectively acylating three hydroxy groups, two primary hydroxy groups and one secondary hydroxy group, among four hydroxy groups in erythritol which is a raw material compound. It is essential to react erythritol at a low temperature in order to differentiate the reactivities of the primary hydroxy group and the secondary hydroxy group. But at such a low temperature, a large amount of solvent is required, because this raw material is scarcely soluble. Further, because the reaction product from this step is a mixture containing tetra-, tri-, di- and mono-acylated compounds, and unreacted compound, purification by column chromatography or the like is indispensable in order to selectively obtain the target triacylated compound. The low yield of this step results in the decrease in the overall yield of the process. In addition, expensive raw materials such as D-erythritol and L-erythritol must be used in order to produce the optically active 2-nitroimidazole derivative.

The 2-nitroimidazole derivative (5) has two asymmetric carbon atoms. Isolation of the optical isomers is so difficult that there have been no reports on the successful isolation of these isomers. Furthermore, nothing have been known at all about the pharmaceutical activities of these optical isomers.

An object of the present invention is therefore to provide optical isomers of 2-nitroimidazole derivative (5) and a drug comprising the same as an effective components.

Other objects of the present invention is to provide a novel process for the preparation of the 2-nitroimidazole derivative (5) and an intermediate for preparing this compound.

DISCLOSURE OF THE INVENTION

In view of this situation, the present inventors have undertaken extensive studies, and found that 2-nitroimidazole derivative and its optical isomers can be obtained at a high yield and industrial advantage, by using tartaric acid diester which is an inexpensive compound as a raw material and by producing an intermediate compound, 2-halomethoxy-1,3,4-triacyloxybutane, by the ring-opening reaction of a dioxolane compound. This finding has led to the completion of the present invention.

Specifically, the present invention provides optically active 2-nitroimidazole derivatives of the following formulas (1) to (4) and a radiosensitizer comprising one of these derivatives as an effective component.

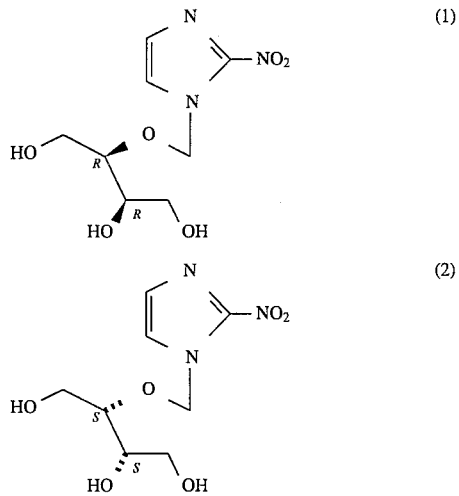

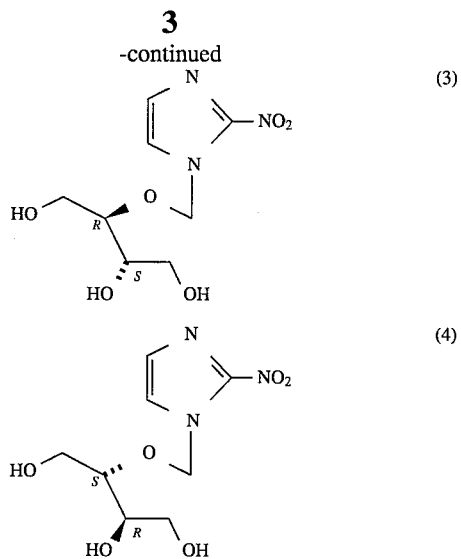

Furthermore, the present invention relates to a process for the preparation of the 2-nitroimidazole derivative according to the following reaction scheme,

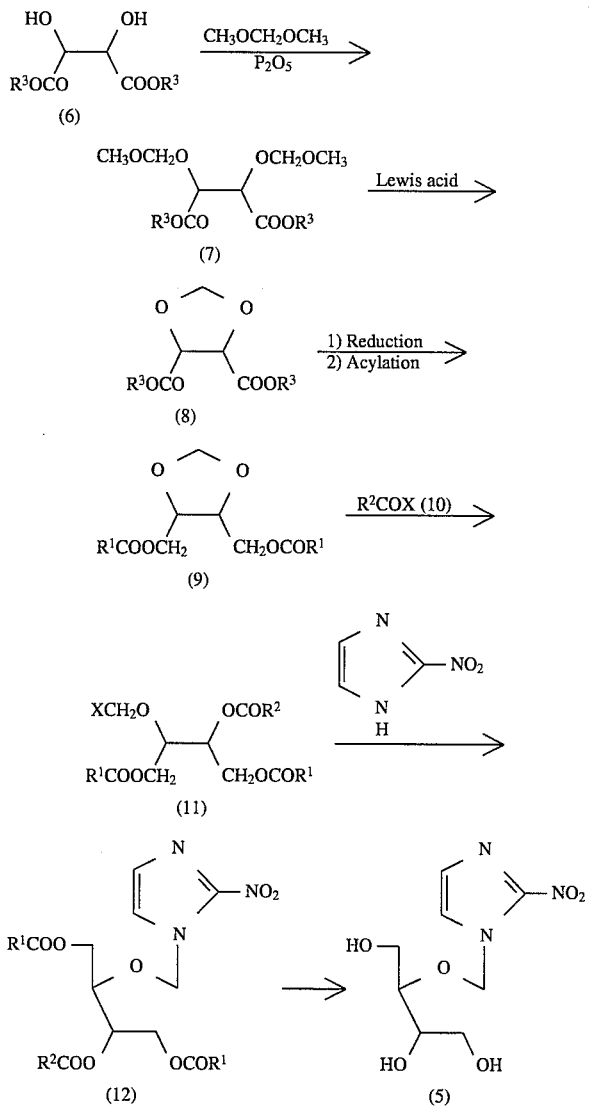

wherein $R^1$, $R^2$, and $R^3$ may be the same or different and each individually represents an aliphatic group or an aromatic group, and X represents a halogen atom; and to an intermediate for the 2-nitroimidazole derivative.

Specifically, the present invention relates to a process for preparing 2-halomethoxy-1,3,4-triacyloxybutane derivative (11) comprising reacting 1,3-dioxolane derivative (9), which is easily obtained from tartaric acid diester (6), and acyl halide (10).

Further, the present invention relates to a process for preparing 2-nitroimidazole derivative (12), which comprises reacting the 2-halomethoxy-1,3,4-triacyloxybutane derivative (11) and 2-nitroimidazole.

Still further, the present invention relates to a process for preparing 2-nitroimidazole derivative (5), which comprises reacting the 2-halomethoxy -1,3,4triacyloxybutane derivative (11) and 2-nitroimidazole, and deacylating the thus-obtained compound (12).

BEST MODE FOR CARRYING OUT THE INVENTION

The present invention will be illustrated according to the reaction scheme presented above.

As aliphatic groups represented by $R^1$, $R^2$, and $R^3$ in the above reaction scheme, linear, branched, or cyclic alkyl or alkenyl groups having 1–24 carbon atoms are given. Specific examples include methyl, ethyl, n-propyl, i-propyl, n-butyl, i-butyl, n-octyl, and palmityl groups. As examples of aromatic groups, phenyl group, naphtyl group, and the like are given. Fluorine, chlorine, bromine, and iodine atoms are given as halogen atoms represented by X.

The reaction for producing compound (7) from compound (6) is preferably carried out by adding phosphorous pentoxide to a mixture of compound (6) and dimethoxymethane, in portions, at room temperature or under heating.

The reaction for producing compound (8) from compound (7) comprises the cyclization of compound (7) by the reaction with a Lewis acid. Boron trifluoride, boron trifluoride etherate, anhydrous zinc chloride, anhydrous aluminum chloride, anhydrous tin chloride, and the like are given as Lewis acids to be reacted with compound (7). The reaction of compound (7) and Lewis acid is carried out by adding a catalytic amount to equivalent amount of Lewis acid to compound (7) at room temperature or under heating while stirring. The reaction of compound (6) and dimethoxymethane may proceed until 1,3-dioxolane derivative (8) is produced by the cyclization reaction, which partially occurs by the action of phosphorous pentoxide. The cyclization reaction may be carried out without separating this 1,3-dioxolane derivative (8) by adding Lewis acid to the reaction mixture.

In order to cyclize a diol compound to produce a 1,3-dioxolane compound, para-formaldehyde, 1,3,5-trioxane, or the like is generally used. In the case of compound (6) these reagents can hardly produce the 1,3-dioxolane ring, resulting in an extremely low yield. The above method, however, can produce 1,3-dioxolane derivative (8) from compound (6) at a high yield of greater than 90%.

The reaction for obtaining compound (9) from compound (8) can be carried out by reducing compound (8) and reacting the reduced product with an aliphatic or aromatic carboxylic acid or a reactive derivative thereof.

A reducing agent such as lithium aluminum hydride or sodium boron hydride can be preferably used for the reducing reaction. Acid halides, acid anhydrides, and the like can be given as examples of the reactive derivatives of aliphatic or aromatic carboxylic acid. The acylation reaction can be carried out preferably according to the conventional method, for example, in the presence of a base such as pyridine at room temperature or under heating.

The reaction of the thus-obtained 1,3-dioxolane derivative (9) and acyl halide (10) can be carried out either in the absence of a catalyst or in the presence of a Lewis acid. This reaction may be also carried out using a solvent or without using a solvent. Benzene, toluene, chloroform, dichloromethane, ethyl acetate, acetonitrile, or the like can be used as a solvent, and anhydrous zinc chloride, anhydrous zinc bromide, stannic chloride, anhydrous aluminum chloride, or the like can be used as the Lewis acid. The reaction temperature is −30° C. to 100° C. Because this reaction is typically exothermic, it is preferably carried out while cooling with water.

The reaction of 2-halomethoxy-1,3,4-triacyloxybutane derivative (11) thus obtained and 2-nitroimidazole is carried out preferably in the presence of a base. Given as examples of the bases are inorganic bases such as sodium carbonate, sodium hydrogen carbonate, potassium carbonate, potassium hydrogen carbonate, cesium carbonate, and sodium hydride; and organic bases such as triethylamine, pyridine, and tributylamine. The reaction is usually carried out in an organic solvent. As the solvents which can be used, polarized solvents such as methanol, ethanol, i-propanol, tetrahydrofuran, dimethylformamide, and dimethylsulfoxide are given. The reaction temperature may be either low or high, with room temperature being preferred.

The deacylation of compound (12) can be carried out according to the conventional method. The compound (5) which is useful as a radiosensitizer can be obtained by this deacylation reaction.

The deacylation reaction can be carried out by the method in which compound (12) is treated for several hours to overnight at 0° C. to room temperature in anhydrous alcohol containing sodium alcolate or in anhydrous alcohol saturated with ammonia gas; a method in which compound (12) is treated at room temperature to 80° C. in a water-alcohol mixture or an organic base such as triethylamine or pyridine; or the like.

After the reaction, the target compound can be separated from the reaction mixture and purified according to conventional methods. For example, in order to separate and purify the target compound, the reaction mixture is concentrated and crystallized or, alternatively, extracted, washed, and concentrated following which the residue is subjected to chromatography or the like.

Compounds (7), (8), (9), (11), (12), and (5) with the steric configuration being retained can be obtained, if the optically active compound (6) is used as the raw material for the reactions of the present invention.

Among the compound of formula (11), compounds of the following formula (11a) having aliphatic groups for $R^{1'}$ and $R^{2'}$ which correspond to $R^1$ and $R^2$ in formula (11), are novel compounds, on which there have been no descriptions in published documents.

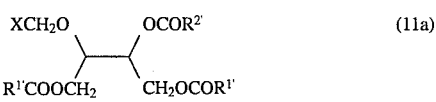
(11a)

Among the optically active 2-nitroimidazole derivatives of the present invention, the compound represented by formula (1) can be prepared from optically active tartaric acid as a starting raw material according to the following reaction formula,

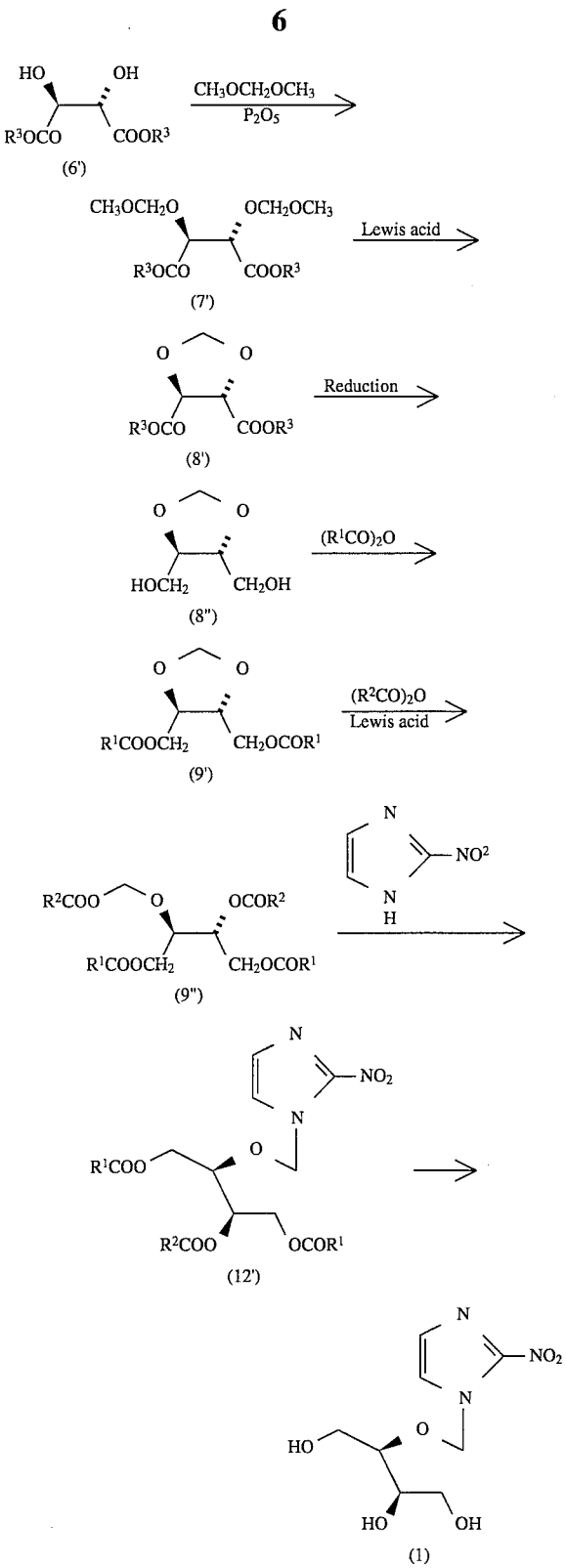

wherein $R^1$, $R^2$, and $R^3$ have the same meanings as previously defined. Specifically, D-(−)-tartaric acid diester (6') is reacted with dimethoxymethane in the presence of phosphorous pentoxide to produce compound (7'). The compound (7') is cyclized by the reaction with Lewis acid to obtain 1,3-dioxolane derivative (8'), which is reduced and acylated into compound (9'). This compound (9') is then reacted with an acid anhydride in the presence of Lewis acid to produce compound (9"). The compound (9") is reacted with 2-nitroimidazole to produce compound (12'), which is deacylated to obtain RR isomer (1).

Each step of the reaction scheme is then illustrated.

The reaction for producing compound (7') from D-(−)-tartaric acid diester (6') can be preferably carried out by adding phosphorous pentoxide in portions to the mixture of the D-(−)-tartaric acid diester (6') and dimethoxymethane at room temperature or under heating.

The reaction for producing 1,3-dioxolane derivative (8') from compound (7') is a cyclization reaction in which compound (7') is reacted with Lewis acid. Boron trifluoride, boron trifluoride etherate, anhydrous zinc chloride, anhydrous aluminum chloride, anhydrous tin chloride, and the like are given as Lewis acids to be reacted with compound (7'). The reaction of compound (7') and Lewis acid is carried out by adding a catalytic amount to equivalent amount of Lewis acid to compound (7') at room temperature or under heating while stirring. The reaction of compound (6') and dimethoxymethane may proceed until 1,3-dioxolane derivative (8') is produced by the cyclization reaction, which partially occurs by the action of phosphorous pentoxide. The cyclization reaction may be completed without separating this 1,3-dioxolane derivative (8') by adding Lewis acid to the reaction mixture.

The reaction for producing compound (9') from 1,3-dioxolane derivative (8') is carried out by reducing the 1,3-dioxolane derivative (8') to obtain compound (8") and reacting this compound (8") with fatty acid anhydride.

A reducing agent such as lithium aluminum hydride or sodium boron hydride can be preferably used for the reducing reaction. The acylation reaction can be preferably carried out according to the conventional method, for example, in the presence of a base such as pyridine at room temperature or under heating.

The reaction of compound (9") and acid anhydride is carried out in the presence of a Lewis acid. Anhydrous zinc chloride, anhydrous zinc bromide, stannic chloride, anhydrous aluminum chloride, or the like can be used as the Lewis acid. This reaction may be carried out using a solvent or without using a solvent. Benzene, toluene, chloroform, dichloromethane, ethyl acetate, acetonitrile, or the like can be used as the solvent. Although the reaction may be carried out either at a low temperature or under heating, room temperature is usually preferred.

The reaction of compound (9") thus obtained and 2-nitroimidazole is carried out in the presence of an acid catalyst by melting these compounds while the pressure is being reduced. As the acid catalyst used in this reaction, protonic acids, such as p-toluenesulfonic acid, methanesulfonic acid, and trichloroacetic acid; and Lewis acids, such as anhydrous zinc chloride, anhydrous aluminum chloride, and anhydrous cupric chloride, can be given. The proportion of compound (9") and 2-nitroimidazole used in the reaction can be arbitrarily determined. Usually, a small excess amount of the former is preferably used. A preferable reaction temperature is usually 50°–150° C., with the reaction time usually between 30 minutes to 6 hours depending on the reaction reagents, solvents, temperature, the type of the acid catalyst, and the like.

The deacylation of compound (12') can be carried out, for example, by the method in which compound (12') is treated for several hours to overnight at 0° C. to room temperature in anhydrous alcohol containing sodium alcolate or in anhydrous alcohol saturated with ammonia gas, a method in which compound (12') is hydrolyzed at room temperature or under heating in a water-alcohol mixture or in an organic base such as triethylamine or pyridine, or the like. A lower alcohol such as methanol, ethanol, or propanol are preferably used as the alcohol.

Among the optically active 2-nitroimidazole derivatives of the present invention, the compound represented by formula (2) can be prepared by using L-(+)-tartaric acid diester instead of D-(−)-tartaric acid diester (6'), as a starting raw material, according to the above reaction formula.

Further, among the optically active 2-nitroimidazole derivatives, the compounds represented by formulas (3) and (4) can be prepared by using meso-tartaric acid diester instead of D-(−)-tartaric acid diester (6'), as a starting raw material, according to the above reaction formula. Alternatively, these may be prepared by benzoylating the three hydroxy groups of racemic 2-nitroimidazole derivative (5) which is obtained by the method described in Japanese Patent Application Laid-open (kokai) No. 110675/1989 and optically resolving the resulting tribenzoate compound, followed by debenzoylation.

The benzoylation of the racemic 2-nitroimidazole derivative (5) can be achieved at a high yield by acting benzoyl chloride in the presence of a base such as pyridine while stirring at room temperature. The racemic tribenzoate isomers obtained here are optically resolved by HPLC using a chiral column to produce the optically active tribenzoate compound. Debenzoylation can be carried out by a method comprising hydrolysis at room temperature in a water-alcohol mixture in the presence of an organic base such as triethylamine, or the like method.

After the reaction, the target compound can be separated from the reaction mixture and purified according to conventional methods. For example, in order to separate and purify the target compound, the reaction liquid is extracted, washed, and concentrated, following which the residue is subjected to chromatography or the like.

The compounds (1) to (4) of the present invention thus obtained exhibited low toxicity and excellent in vivo and in vitro radiosensitizing activity as shown in test examples hereinafter, and thus are useful as a radiosensitizer to be used in radiotherapy of cancers.

It is preferable that the radiosensitizer of the present invention be administered five minutes to five hours prior to the time when radiation is given to a subject. Either oral or non-oral administration is acceptable. The composition can be prepared into tablets, capsules, granules, powder, suppositories, or injection, after the addition of suitable additives such as excipients, stabilizers, preservatives, and buffering agents. A dose is dependednt on the age, location of cancers, types of cancers, symptoms, and the like, with an amount of 0.2 to 5 $g/m^2$ body surface area being usually preferable.

EXAMPLES

The present invention is hereinafter illustrated more specifically by way of examples, which should not be construed as limiting the present invention.

Example 1

Synthesis of diethyl (S,S)-bis(O-methoxymethyl)tartarate 25.76 g of diethyl D-(−)-tartarate was mixed with and completely dissolved in 50 ml of dimethoxymethane. Phosphorous pentoxide was added to the solution in portions while stirring at room temperature to effect the reaction. While monitoring the reaction by TLC (developer, CHCl$_3$:CH$_3$OH=19:1; detection by iodine), phosphorous pentoxide was added until a single spot of Rf 0.88 developed. After the reaction, the reaction mixture was transferred to a separating funnel and extracted with 700 ml of a 5:1 mixed solution of ethyl acetate and benzene. The extract was washed with water and saturated aqueous solution of sodium chloride, dried over anhydrous sodium sulfate, and filtered, followed by removal of the solvent by evaporator to obtain the title compound as an oily substance.

MS: 294(M$^+$)
NMR(CDCl$_3$)δ:
1.30(6H, t, —OCH$_2$C$\underline{H}_3$×2),
3.34(6H, s, —OC$\underline{H}_3$×2),
4.16–4.30(4H, m, —OC$\underline{H}_2$CH$_3$×2),
4.66–4.79(6H, m, >C$\underline{H}$O—×2 and —OC$\underline{H}_2$OCH$_3$×2)

Example 2

Synthesis of
(4S,5S)-4,5-bis(ethoxycarbonyl)-1,3-dioxolane

To a solution of 30.07 g of diethyl (S,S)-bis(O-methoxymethyl)tartarate obtained in Example 1 in 300 ml of benzene was added 16.12 g of boron trifluoride etherate, and the mixture was stirred at room temperature to react. After the reaction overnight, the reactant was extracted with the addition of 500 ml of ethyl acetate. The extract was neutralized with saturated aqueous solution of sodium hydrogen carbonate, washed with water and saturated aqueous solution of sodium chloride, and dried over anhydrous sodium sulfate. After filtration, the solvent was evaporated. Although it was possible to use this product as is for the next reaction, the title compound was obtained almost quantitatively as a colorless transparent oil when purified by silica gel column chromatography.

MS: 218(M$^+$)
NMR(CDCl$_3$)δ:
1.31(6H, t, —CH$_2$C$\underline{H}_3$×2),
4.26(4H, q, —C$\underline{H}_2$CH$_3$×2),
4.76(2H, s, >C$\underline{H}$O— ×2),
5.26(2H, s, —OC$\underline{H}_2$O— ×2)

Example 3

Synthesis of
(4R,5R)-4,5-bis(hydroxymethyl)-1,3-dioxolane 300 ml of diethyl ether was added to 25.75 g of lithium aluminum hydride, and the mixture was heated while refluxing. A solution of 130.46 g of (4S,5S)-4,5-bis (ethoxycarbonyl)-1,3-dioxolane (obtained in Example 2) in 100 ml of ether was slowly added dropwise to this mixture. After the addition, the refluxing was continued for further about one hour. After allowing the reaction mixture to cool, 30 ml of water was slowly added under ice-cooling to decompose an excessive amount of lithium aluminum hydride. Then, 30 ml of 4N aqueous solution of sodium hydroxide and 90 ml of water were added dropwise. The reaction mixture was filtered with suction and the precipitate was extracted with 1000 ml of an ethanol-dioxane mixture at about 60° C., followed by filtration of the extract with suction. This procedure was repeated three times. The filtrate was concentrated to obtain crude (4R,5R)-4,5-bis(hydroxymethyl)-1,3-dioxolane.

Example 4

Synthesis of
(4R,5R)-4,5-bis(acetoxymethyl)-1,3-dioxolane

The crude (4R,5R)-4,5-bis(hydroxymethyl)-1,3dioxolane obtained in Example 3 was dissolved in 300 ml of pyridine. After the addition of 150 g of excessive amount of acetic anhydride under ice cooling, the mixture was reacted for about 16 hours while stirring at room temperature. 20 ml of ethanol was added in portions while cooling over a water bath in order to decompose the excessive amount of acetic anhydride. After concentration by evaporator, the concentrate was extracted with 500 ml of ethyl acetate and washed with water, followed by removal of the solvent by evaporator. Although this product may be used for the next reaction as it was, the purification by silica gel column chromatography afforded 79.29 g of light yellow oil of (4R,5R)-4,5-bis(acetoxymethyl)-1,3-dioxolane.

MS: 218(M$^+$)
NMR(CDCl$_3$)δ:
2.11(6H, s, —COC$\underline{H}_3$×2),
4.00–4.04(2H, m, >C$\underline{H}$O— ×2),
4.21–4.23(4H, d, —C$\underline{H}_2$OCO— ×2),
5.06(2H, s, —OC$\underline{H}_2$O—)

Example 5

Synthesis of
(2R,3R)-2-bromomethoxy-1,3,4-triacetoxybutane

A mixture of 25.0 g of acetyl bromide and 42.0 g of (4R,5R)-4,5-bis(acetoxymethyl)-1,3-dioxolane obtained in Example 4 was stirred under cooling with ice, and 1.0 g of anhydrous zinc chloride was added to it. After the reaction for 30 minutes, the ice water bath was dismantled and the mixture was stirred for a further one hour while stirring at room temperature. After the reaction, 50 ml of benzene was added to separate insoluble matters by filtration, and the benzene was evaporated at a low temperature (below room temperature). No peaks for the raw material were observed at all by NMR analysis of the reaction product, indicating that the decylization occurred quantitatively and the title compound was produced.

NMR(CDCl$_3$)δ:
2.0–2.2(9H, —COC$\underline{H}_3$×3),
4.0–4.4(5H, —C$\underline{H}_2$OAc ×2, >C$\underline{H}$OCH$_2$—),
5.3(1 H, >C$\underline{H}$OCO—),
5.7–5.8(2H, —OC$\underline{H}_2$Br)

Example 6

Synthesis of (1'R,2'R)-1-[(1'-acetoxymethyl-2', 3'-diacetoxy)propoxy]methyl-2-nitroimidazole 21.5 g of 2-nitroimidazole, 20.0 g of triethylamine, and 50 ml of dimethylformamide were added to all the amount of the crude (2R,3R)-2-bromomethoxy-1,3,4-triacetoxybutane obtained in Example 5. The reaction was exothermic, producing white precipitate of triethylamine hydrobromide. The mixture was cooled to control the reaction temperature below 40° C. The reaction was continued for a further several hours at room temperature while stirring. The produced hydrobromide was filtered with suction and the precipitate was washed with ethyl acetate. The filtrate and washings were combined and concentrated by evaporator.

After evaporating almost all dimethylformamide, the residue was extracted with the addition of ethyl acetate. The ethyl acetate layer was washed thoroughly with saturated aqueous solution of sodium hydrogen carbonate until there was no yellow color of 2-nitroimidazole. This product was then washed with water, dried, concentrated, and purified by silica gel column chromatography (eluent: 9:1 mixture of benzene and ethyl acetate) to obtain 49.7 g (yield: 70.0%) of the title compound.

MS: 373($M^+$)

NMR(CDCl$_3$)δ:

2.0–2.2(9H, —COC$\underline{H}_3$×3), 4.0–4.4(5H, m, —C$\underline{H}_2$OCO— ×2, >C$\underline{H}$OCH$_2$—), 5.1–5.2(1H, m, >C$\underline{H}$OCO—), 5.8–6.1(2H, nq, —OC$\underline{H}_2$N (ring)), 7.2–7.3(d×2, ring proton)

Example 7

Synthesis of (1'R,2'R)-1-[(2', 3'-dihydroxy-1'-hydroxymethyl)propoxy]methyl-2-nitroimidazole 11.58 g of (1'R,2'R)-1-[(1'-acetoxymethyl-2',3'-diacetoxy)propoxy]methyl-2-nitroimidazole obtained in Example 6 was dissolved in 100 ml of methanol and the mixture was stirred at room temperature. 10 ml of triethylamine and 20 ml of water were added to effect the hydrolysis while stirring. After confirming the completion of the reaction by TLC (developer: chloroform:methanol=9:1; detection by UV absorption), the solvent was evaporated and the residue was crystallized. The crystals were recrystallized from ethanol to obtain 4.30 g of yellowish white crystals of the title compound.

m.p.: 99°–101.5° C.

MS(m/e): 248(M+1)

NMR(DMSO)δ:

3.25–3.33(2H, m, —CH(OH)CH$_2$OH), 3.39–3.64(4H, m, —C$\underline{H}$×2 and —CH(OCH$_2$—)C$\underline{H}_2$OH), 4.46(1H, t, —CH(OH)CH$_2$O$\underline{H}$), 4.59(1H, —CH(O$\underline{H}$)—), 4.64(1H, —CH(OCH$_2$—)CH$_2$O$\underline{H}$), 5.88(2H, nq, —CH$_2$N (ring)), 7.21(1H, S, ring proton), 7.83(1H, S, ring proton)

IR(cm$^{-1}$): 3385(OH), 1540(NO$_2$), 1370(NO$_2$)

Optical rotation: $[α]_D^{25}$=−12.09° (c=1.0, MeOH) $[α]_D^{20}$=−9.2° (c=2.0, H$_2$O)

Example 8

Synthesis of (2RS,3SR)-2-acetoxy-3-bromomethoxy-1,4-dibenzoyloxybutane 34.2 g of (4RS,5SR)-4,5-bis(benzoyloxymethyl)-1,3-dioxolane and acetyl bromide were mixed with stirring under cooling with ice. The mixture was further reacted with the addition of 1.0 g of zinc bromide. After dismantling the ice water bath, 50 ml of dichloromethane was added and reacted while stirring at room temperature. After the reaction for two hours, the insoluble matters were separated by filtration, and the filtrate was concentrated by evaporator at a low temperature (below room temperature) to obtain the title compound.

NMR(CDCl$_3$)δ:

4.0–4.7(5H, m, —C$\underline{H}_2$OBz×2, >C$\underline{H}$OCH$_2$), 5.2(1H, m, >C$\underline{H}$OCO—), 5.7(2H, s, —OCH$_2$Br), 7.2–8.1(10H, m, Aromatic)

Example 9

Synthesis of (1'S,2'S)-1-[(1'-acetoxymethyl-2', 3'-diacetoxy)propoxy]methyl-2-nitroimidazole 17.0 g of (2S,3S)-2-bromomethoxy-1,3,4-triacetoxybutane, 5.7 g of 2-nitroimidazole, 8.8 g of potassium carbonate, and 100 ml of ethyl alcohol were mixed and reacted at room temperature overnight while stirring. The insoluble matters were separated by filtration, the filtrate was concentrated by evaporator, and 100 ml of ethyl acetate was added to the residue, followed by mixing. After separating the insoluble matters by filtration, the filtrate was washed thoroughly with saturated aqueous solution of sodium hydrogen carbonate until there was no yellow color of 2-nitroimidazole. This product was then washed with water and dried. After evaporating the solvent, the residue was purified by silica gel column chromatography (eluent: 9:1 mixture of benzene and ethyl acetate) to obtain 7.9 g (yield: 43.0%) of the title compound.

MS: 373($M^+$)

NMR(CDCl$_3$)δ:

2.0–2.2(9H, s×3, —COC$\underline{H}_3$×3), 4.0–4.4(5H, m, —C$\underline{H}_2$OCO— ×2, >C$\underline{H}$OCH$_2$—), 5.1–5.2(1H, m, —C$\underline{H}$—OCO—), 5.8–6.1(2H, nq, —OC$\underline{H}_2$N (ring)), 7.2–7.3(d×2, ring proton )

Example 10

Synthesis of (1'S,2'S)-1-[(2', 3'-dihydroxy-1'-hydroxymethyl)propoxy]methyl-2-nitroimidazole 68.9 g of (1'S,2'S)-1-[(1'-acetoxymethyl-2', 3'-diacetoxy)propoxy]methyl-2-nitroimidazole obtained in Example 9 was mixed with and dissolved in 200 ml of methanol. After the addition of 100 g of triethylamine, the mixture was stirred at room temperature. Then, 30 ml of water was added, followed by stirring overnight to effect the hydrolysis. After confirmation of completion of the reaction by TLC (developer: ethyl acetate, detection by UV), the reaction mixture was concentrated by evaporator. The concentration by evaporation was repeated with the addition of isopropanol and toluene, until the produced acetic acid and triethylamine were completely removed. The residue was dissolved in 50 ml of ethanol, filtered through glass filter, and crystallized with the addition of crystal seeds. After separation by filtration, the crystals were dried to obtain 26.2 g (yield: 57.0%) of the title compound as light yellow crystals.

m.p.: 97°–98° C.

MS: 248($M^+$)

NMR(DMSO)δ:

3.2–3.7(6H, m, —CH$_2$OH×2, >C$\underline{H}$O— ×2), 4.50(1H, t, —CH$_2$O$\underline{H}$), 4.6–4.7(2H, m, —CH$_2$O$\underline{H}$ and >CHO$\underline{H}$), 5.85(2H, nq, —OCH$_2$N (ring)),
7.18(1H, d, ring proton),
7.80(1H, d, ring proton)
Optical rotation: $[\alpha]_D^{25}$=+12.2° (c=1.0, CH$_3$OH) $[\alpha]_D^{20}$=+9.4° (c=2.0, H$_2$O)
Optical purity: 99.5% ee
Elemental analysis
Found (%): C;16.93 H;38.88 N;5.35
Calculated (%): C;17.00 H;38.87 N;5.30

Example 11

Synthesis of
(2R,3R)-2-acetoxymethoxy-1,3,4-triacetoxybutane 100 ml of acetic anhydride was added to 70.12 g of (4R,5R)-4,5-bis(acetoxymethyl)-1,3-dioxolane obtained in Example 4 and mixed at room temperature to dissolve. After the addition of 3.05 g of anhydrous zinc chloride and 10 ml of glacial acetic acid, the mixture was stirred overnight. The resultant reaction mixture was extracted with 700 ml of ethyl acetate, neutralized with saturated aqueous solution of sodium hydrogen carbonate, washed with water and saturated aqueous solution of sodium chloride, dried over anhydrous sodium sulfate, and filtered. The solvent was removed by evaporation to obtain 99.48 g of the title compound as a reddish brown oil.

MS: 320(M$^+$)
NMR(CDCl$_3$)δ:
2.07(3H, s, —COCH$_3$),
2.09(3H, s, —COCH$_3$),
2.01(3H, s, —COCH$_3$),
2.12(3H, s, —COCH$_3$),
4.04–4.38(5H, m, —CH$_2$OCO×2 and >CHOCH$_2$—),
5.21–5.27(1H, m, >CHOCO—),
5.31(2H, s, —OCH$_2$O—)

Example 12

Synthesis of diethyl
(2R,3R)-bis(O-methoxymethyl)tartarate 20.6 g of diethyl L-(+)-tartarate was mixed with and completely dissolved in 60.8 g of dimethoxymethane. The mixture was reacted with the addition of phosphorous pentoxide in portions while stirring at room temperature. While monitoring the reaction by TLC (developer, benzene:ethyl acetate=3:2; detection by iodine), phosphorous pentoxide was added until a single spot of Rf 0.63 developed. After the reaction, the supernatant was transferred to a separating funnel and extracted with 200 ml of ethyl acetate. The extract was washed with saturated aqueous solution of sodium hydrogen carbonate, and then water several times, dried, concentrated by evaporator, and purified by silica gel column chromatography (eluent: benzene) to obtain 23.7 g (yield: 80.8%) of the title compound.

MS: 294(M$^+$)
NMR(CDCl$_3$)δ:
1.32(6H, t, —CH$_3$×2),
3.35(6H, s, —OCH$_3$×2),
4.25(4H, m, —CH$_2$CH$_3$×2),
4.6–4.9(6H, m, —OCH$_2$OCH$_3$×2 and >CHOCH$_2$—×2)

Example 13

Synthesis of
(4R,5R)-4,5-bis(ethoxycarbonyl)-1,3-dioxolane 23.7 g of diethyl (2R,3R)-bis(O-methoxymethyl)tartarate obtained in Example 12 was dissolved in 50 ml of benzene and reacted with the addition of 11.5 g of boron trifluoride etherate while stirring. After the reaction overnight at room temperature, the resultant reaction mixture was transferred to a Separating funnel and extracted with 200 ml of ethyl acetate. The extract was neutralized with saturated aqueous solution of sodium hydrogen carbonate, washed with water, dried, and concentrated by evaporator. Although it was possible to use this product as it was for the next reaction, the product was purified by eluting with benzene using silica gel column to obtain 17.6 g (yield: 99.8 g) of the title compound.

MS: 218(M$^+$)
NMR(CDCl$_3$)δ:
1.35(6H, t, —CH$_2$CH$_3$×2),
4.30(4H, q, —CH$_2$CH$_3$×2),
4.75(2H, s, >CHO— ×2),
5.25(2H, s, —OCH$_2$O—)

Example 14

Synthesis of
(4S,5S)-4,5-bis(hydroxymethyl)-1,3-dioxolane 300 ml of tetrahydrofuran was added dropwise to 43.61 g of lithium aluminum hydride while cooling with ice. To this was added dropwise a solution of 125.3 g of (4R,5R)-4,5-bis(ethoxycarbonyl)-1,3-dioxolane prepared in Example 13 in 200 ml of tetrahydrofuran and reacted while vigorously stirring under cooling with ice. After the addition, the mixture was reacted for one hour while refluxing. Then, water was added drop by drop to hydrolyze lithium aluminum hydride under cooling with ice. After the addition of 0.5 ml of 4 mol/l sodium hydroxide dropwise, the mixture was stirred for 30 minutes and filtered with suction. 700 ml of ethanol was added to the precipitate, and the mixture was heated at 60°–70° C., stirred, and filtered with suction. This procedure was repeated three times. All filtrates were combined and concentrated by evaporator to obtain a crude title compound.

Example 15

Synthesis of
(4S,5S)-4,5-bis(acetoxymethyl)-1,3-dioxolane 200 ml of pyridine was added to crude (4S,5S)-4,5-bis(hydroxymethyl)-1,3-dioxolane obtained in Example 14 to dissolve the latter. An excessive amount of acetic anhydride (200 g) was added dropwise under cooling with ice. After several hours of reaction, ethyl alcohol was added dropwise to decompose the excessive acetic anhydride. The reaction mixture was concentrated by evaporator to remove almost all pyridine. The concentrate was extracted with the addition of 500 ml of ethyl acetate. The extract was washed with saturated aqueous solution of sodium hydrogen carbonate, then with water, dried, and concentrated by evaporator. The residue was purified by silica gel column chromatography (eluent, benzene:ethylacetate=9:1) to obtain 90.0 g of the title compound as a colorless liquid.

MS: 218(M$^+$)

NMR(CDCl$_3$)δ:
2.10(6H, s, C$\underline{H_3}$CO— ×2),
4.02(2H, m, >C$\underline{H}$O— ×2),
4.25(4H, m, —C$\underline{H_2}$CO— ×2),
5.05(2H, s, —OC$\underline{H_2}$O—)

Example 16

Synthesis of (2S,3S)-2-acetoxymethoxy-1,3,4-triacetoxybutane 100.2 g of acetic anhydride was added to 61.0 g of (4S,5S)-4,5-bis(acetoxymethyl)-1,3-dioxolane obtained in Example 15. To this was added 11.8 g of glacial acetic acid to dissolve the mixture. 3.4 g of anhydrous zinc chloride was added while stirring. The zinc chloride was slowly dissolved to change the color of the mixture from yellow into charcoal. After the reaction overnight, the reaction mixture was charged into a separating funnel which contained 500 ml of ethyl acetate. To this was added saturated aqueous solution of sodium hydrogen carbonate to neutralize. After washing with water and drying, the product was concentrated by evaporator. Acetic anhydride not decomposed was removed by a chemical pump to obtain 91.9 g (yield: 87.7%) of an yellow oil of the title compound.

MS: 320(M$^+$)
NMR(CDCl$_3$)δ:
2.05–2.15(12H, s×4, C$\underline{H_3}$CO— ×4),
4.1–4.4(5H, m, —C$\underline{H_2}$O— × 2, >C$\underline{H}$OCH$_2$—),
5.25(1H, m, >C$\underline{H}$OCO—),
5.35(2H, s, —OC$\underline{H_2}$O—)

Example 17

Synthesis of diethyl (2RS,3SR)-bis(O-methoxymethyl)tartarate 20.6 g of diethyl meso-tartarate was mixed with and completely dissolved in dimethoxymethane. The mixture was reacted with the addition of phosphorous pentoxide in portions while stirring at room temperature. While monitoring the reaction by TLC (developer, benzene:ethyl acetate= 3:2; detection by iodine), phosphorous pentoxide was added until a single spot of Rf 0.62 was developed. After the reaction, the reaction mixture was transferred to a separating funnel and extracted with 200 ml of ethyl acetate. The extract was washed with saturated aqueous solution of sodium hydrogen carbonate, and then with water, dried over anhydrous sodium sulfate, and filtered. The solvent was removed by evaporator to obtain the title compound as an oily substance.

MS: 294(M$^+$)
NMR(CDCl$_3$)δ:
1.35(6H, t, —OCH$_2$C$\underline{H_3}$×2),
3.45(6H, s, —OC$\underline{H_3}$×2),
4.1–4.4(4H, m, —OC$\underline{H_2}$CH$_3$×2),
4.6–4.9(6H, m, >C$\underline{H}$O— ×2 and —OC$\underline{H_2}$OCH$_3$×2)

Example 18

Synthesis of (4RS,5SR)-4,5-bis(ethoxycarbonyl)-1,3-dioxolane 29.4 g of diethyl (2RS,3SR)-bis(O-methoxymethyl)tartarate obtained in Example 17 was dissolved in 100 ml of benzene and reacted with the addition of 14.2 g of boron trifluoride etherate while stirring at room temperature. After the reaction overnight, the resultant reaction mixture was extracted with 200 ml of ethyl acetate. The extract was neutralized with saturated aqueous solution of sodium hydrogen carbonate, washed with water, dried over anhydrous sodium sulfate, and filtered, followed by evaporation of the solvent. Although it was possible to use this product as it was for the next reaction, the product was purified by silica gel column chromatography to quantitatively obtain the title compound as a colorless transparent oil.

MS: 218(M$^+$)
NMR(CDCl$_3$)δ:
1.35(6H, t, —CH$_2$C$\underline{H_3}$×2),
4.25(4H, q, —C$\underline{H_2}$CH$_3$×2),
4.80(2H, s, >C$\underline{H}$O— ×2),
5.2(1H, s, —OC$\underline{H_2}$O—),
5.4(1H, s, —C$\underline{H_2}$O—)

Example 19

Synthesis of (4RS,5SR)-4,5-bis(hydroxymethyl)-1,3-dioxolane 100 ml of tetrahydrofuran was added to 11.4 g of lithium aluminum hydride, and the mixture was heated while refluxing. To this was added dropwise a solution of 21.8 g of (4RS,5SR)-4,5-bis(ethoxycarbonyl)-1,3-dioxolane prepared in Example 18 in 30 ml of tetrahydrofuran. After the addition, the mixture was reacted for one hour while refluxing. After allowing to cool, 30 ml of water was slowly added while cooling with ice to hydrolyze excessive lithium aluminum hydride. Then, 30 ml of 4N aqueous solution of sodium hydroxide and 90 ml of water was added dropwise. The mixture was filtered with suction, following which the precipitate was extracted with 1000 ml of ethanol-dioxane mixture at 60° C. and filtered with suction. This procedure was repeated three times. All filtrates were concentrated by evaporator to obtain a crude title compound.

Example 20

Synthesis of (4RS,5SR)-4,5-bis(acetoxymethyl)-1,3-dioxolane (4RS,5SR)-4,5-bis(hydroxymethyl)-1,3-dioxolane obtained in Example 19 was dissolved in 100 ml of pyridine. An excessive amount of acetic anhydride (30.6 g) was added under cooling with ice. After reacting for about four hours at room temperature, 10 ml of ethyl alcohol was added dropwise under cooling with ice to decompose the excessive acetic anhydride. The reaction mixture was concentrated by evaporator. The concentrate was extracted with the addition of 300 ml of ethyl acetate, the extract was washed with water, and the solvent was removed by evaporator. Although it was possible to use this product in the next step as it was, the residue was purified by silica gel column chromatography (eluent, benzene:ethylacetate=95:5) to obtain 18.5 g (yield: 85.0%) of the title compound as a light yellow oil.

MS: 218(M$^+$)
NMR(CDCl$_3$)δ:
2.15(6H, s, —COC$\underline{H_3}$×2),
4.1–4.2(2H, m, >C$\underline{H}$O— ×2),
4.3–4.4(4H, d, —C$\underline{H_2}$OCO ×2),
4.9(1H, s, —OC$\underline{H_2}$O—),
5.2(1H, s, —OC$\underline{H_2}$O—)

Example 21

Synthesis of (2RS,3SR)-2-acetoxymethoxy-1,3,4-triacetoxybutane 20 ml of acetic anhydride was added to 12.2 g of (4RS,5SR)-4,5-bis(acetoxymethyl)-1,3-dioxolane obtained in Example 20. The mixture was mixed to dissolution at room temperature. To this were added 0.7 g of anhydrous zinc chloride and 2 ml of glacial acetic acid. The mixture was stirred overnight at room temperature and extracted with 300 ml of ethyl acetate. The extract was neutralized with saturated aqueous solution of sodium hydrogen carbonate. After washing with water and drying over anhydrous sodium sulfate, the product was filtered and the solvent was evaporated to obtain 19.0 g (yield: 92.0%) of the title compound.

MS: 320($M^+$)

NMR(CDCl$_3$)δ:

2.08(3H, s, —COC$\underline{H}_3$), 2.09(3H, s, —COC$\underline{H}_3$)

2.10(3H, s, —COC$\underline{H}_3$), 2.11(3H, s, —COC$\underline{H}_3$), 4.1–4.5(5H, m, —C$\underline{H}_2$OCO ×2 and >C$\underline{H}$OCH$_2$— ), 5.1–5.2(1H, m, >C$\underline{H}$O—CO—), 5.32(2H, q, —OC$\underline{H}_2$O—)

Example 22

Synthesis of (1'RS,2'SR)-1-[(1'-acetoxymethyl-2', 3'-diacetoxy)propoxy]methyl-2-nitroimidazole 8.4 g of 2-nitroimidazole and a catalytic amount (0.2 g) of para-toluenesulfonic acid were added to 23.8 g of (2RS, 3SR)-2-acetoxymethoxy-1,3,4-triacetoxybutane obtained in Example 21. The mixture was slowly heated with stirring, while removing acetic acid produced in the reaction by suction using an aspirator. The acetic acid started to evaporate at the oil bath temperature of 80°–90° C. The evaporation almost terminated at 140° C. indicating the completion of the reaction, whereupon the reaction mixture was allowed to cool and extracted with 100 ml of a solvent. The extract was washed thoroughly with saturated aqueous solution of sodium hydrogen carbonate until there was no yellow color in washings due to 2-nitroimidazole. Then, the product was washed with water, dried over anhydrous sodium sulfate, and filtered. The solvent was evaporated and the residue was purified by silica gel column chromatography (eluent, benzene:ethylacetate=9:1) to obtain 13.8 g (yield: 50.0%) of light yellow oil of the title compound.

MS: 373($M^+$)

NMR(CDCl$_3$)δ:

2.03(3H, s, —C$\underline{H}_3$)

2.05(3H, s, —C$\underline{H}_3$), 2.08(3H, s, —C$\underline{H}_3$), 3.95–4.50(5H, m, —C$\underline{H}_2$OCO × 2 and >C$\underline{H}$OCH$_2$—), 5.05–5.15(1H, m, >C$\underline{H}$OCO—), 5.90(2H, s, >CHOC$\underline{H}_2$—), 7.20(1H, s, ring proton), 7.30(1H, s, ring proton)

Example 23

Synthesis of (1'RS,2'SR)-1-[(2',3'-dihydroxy-1'-hydroxymethyl)propoxy]methyl-2-nitroimidazole 6.9 g of (1'RS,2'SR)-1-[(1'-acetoxymethyl-2', 3'-diacetoxy)propoxy]methyl-2-nitroimidazole obtained in Example 22 was dissolved in 30 ml of methanol, and stirred at room temperature. After the addition of 10 ml of triethylamine and 5 ml of water, the mixture was stirred to effect the hydrolysis. After confirmation of completion of the reaction by TLC (developer: ethyl acetate, detection by UV), the solvent was evaporated and the residue was crystallized. 2.6 g (yield: 57.0%) of yellow crystals of the title compound was obtained by recrystallization from ethanol.

m.p.: 136.0°–137.0° C.

MS: (m/e): 284(M+1)

NMR(DMSO)δ:

3.15–3.70(6H, m, —C$\underline{H}$(OH)C$\underline{H}_2$OH, —C$\underline{H}$×2 and —C$\underline{H}$(OCH$_2$—)C$\underline{H}_2$OH), 4.40(1H, t, —CH(OH)CH$_2$O$\underline{H}$), 4.75(1H, d—CH(O$\underline{H}$)—), 4.65(1H, t, —CH(OCH$_2$—)CH$_2$O$\underline{H}$), 5.85(2H, s, —OC$\underline{H}_2$N (ring)), 7.15(1H, s, ring proton), 7.80(1H, s, ring proton)

IR(cm$^{-1}$): 3385(OH), 1540(NO$_2$), 1370(NO$_2$)

Example 24

Synthesis of (1'R,2'S)/(1'S,2'R)-1-[(1'-benzoyloxymethyl -2', 3'-dibenzoyloxy)propoxy]methyl-2-nitroimidazole 100 ml of pyridine was added to 4.59 g of (1'RS, 2'SR)-1-[(2', 3'-dihydroxy-1'-hydroxymethyl) propoxy]-methyl-2-nitroimidazole prepared in Example 23. To the mixture was added dropwise 10 ml of benzoyl chloride while stirring over a water bath. After stirring overnight, the solvent was evaporated and the residue was extracted with 500 ml of a 4:1 mixture of ethyl acetate and benzene. The extract was washed with water, d-HCl, saturated aqueous solution of sodium hydrogen carbonate, water, and saturated aqueous solution of sodium chloride, dried over anhydrous sodium sulfate, and filtered. The solvent was evaporated and the residue was purified by silica gel column chromatography (benzene-ethyl acetate) to obtain a quantitative amount of the title compounds as a light yellow oil.

These compounds were optically resolved by HPLC using a chiral column (AS 0.46 φ×2.5L) to isolate the optically active compounds (tribenzoate compounds of formulas (3) and (4)).

MS: 559($M^+$)

NMR(CDCl$_3$)δ:

3.42–4.85(5H, m, —C$\underline{H}_2$OCO×2 and —C$\underline{H}$(OCH$_2$—)CH$_2$—), 5.68–5.73(1H, m, —C$\underline{H}$(OCO—)CH$_2$—), 5.95–6.07(2H, nq, —OC$\underline{H}_2$N (ring)), 7.00(1H, d, imidazole ring proton), 7.27(1H, d, imidazole ring proton), 7.39–7.48(6H, m, m-benzene ring proton), 7.53–7.62(3H, m, p-benzene ring proton), 7.93–8.02(6H, m, o-benzene ring proton)

Example 25

Synthesis of (1'R,2'S)/(1'S,2'R) -1-[(2', 3'-dihydroxy-1'-hydroxymethyl)propoxy] propoxy]methyl-2-nitroimidazole 15.99 g of one of the optically resolved compounds among (1'R,2'S)/(1S,2'R)-1-[(1'-benzoyloxymethyl-2', 3'-dibenzoyloxy)propoxy]methyl-2-nitroimidazole of Example 24 was dissolved in 150 ml of ethanol and 10 ml of ethyl acetate, and the solution was stirred at room temperature. To the mixture were added 50 ml of water and 15 ml of triethylamine, followed by stirring to effect hydrolysis. After confirmation of completion of the reaction by TLC (developer: chloroform:methanol =19:1), the solvent was evaporated and the residue was crystallized. Another resolved compound was also treated in the same manner to obtain crystals. These were respectively recrystallized to obtain the title compounds as white needles.

m.p.: 129°–130.5° C.

MS: 248(M+1)

NMR(DMSO)δ:
3.16–3.63(6H, m, >C$\underline{H}$O— ×2 and —C$\underline{H}_2$OH×2),
4.22(1H, t, —CH(OH)CH$_2$O$\underline{H}$),
4.95(1H, t, —CH(OCH$_2$—)CH$_2$O$\underline{H}$),
4.68(1H, d, —CHO$\underline{H}$—),
5.83(2H, nq, —OC$\underline{H}_2$N (ring)),
7.19(1H, d, ring proton),
7.78(1H, d, ring proton)

Optical rotation: (1'R*, 2'S*): $[\alpha]_D^{20}$=+4.7° (c=2, H$_2$O)
(1'S*, 2'R*): $[\alpha]_D^{20}$=−4.5° (c=2, H$_2$O)

IR(cm$^{-1}$): 3315(OH), 1545(NO$_2$), 1365(NO$_2$)

Test Example 1

In vitro hypoxic cell sensitization effect

The SR-RS racemate is known to exhibit about the same degree of hypoxic cell radiosensitization effect as misonidazole (Japanese Patent Application Laid-open (kokai) No. 223258/1991). The degree of the hypoxic cell radiosensitization effects of optical isomers of the present invention as compared with the racemate was studied by the in vitro assay.

Specifically, the radiosensitization effects were investigated using breast carcinoma cell EMT6/KU derived from Balb/c mouse. A hypoxic cell suspension was prepared from MEM suspension-containing EMT6/KU cells at a concentration 4×10$^5$ cells/ml by adding the test compound to a final concentration of 1 mM, and gently shaking it under a nitrogen gas stream containing 5% CO$_2$ for one hour at room temperature. Gamma-ray was irradiated to the suspension and a radiation-survival rate curve was developed by the colony formation method. The sensitization rate was determined from this radiation-survival rate curve by dividing (i) the amount of radiation which decreases the survival rate of the hypoxic cells by 1% when no test compound was added by (ii) the amount of radiation which decreases the survival rate of the hypoxic cells by 1% when the test compound was added. The results are shown in Table 1.

TABLE 1

| Sample | Hypoxic cell sensitization rate |
| --- | --- |
| RS-SR racemate | 1.7 |
| SS isomer | 1.8 |
| RR isomer | 1.8 |
| RS or SR isomer (rotation(+)) | 1.7 |
| RS or SR isomer (rotation(−)) | 1.7 |

As can be seen in Table 1, the optical isomers of the present invention have the same degree of excellent hypoxic cell radiosensitization effects as the racemate, indicating their effectiveness for the radiation therapy of cancer.

Test Example 2

In vivo-in vitro hypoxic cell sensitization effect

The degree of the hypoxic cell radiosensitization effects of optical isomers of the present invention in in vivo-in vitro system was investigated in the same manner using the racemate as a control. Specifically, the radiosensitization effects were investigated using EMT6/KU-cancerated Balb/c mouse. 200 mg/kg of each test compound was administered and 20 Gy gamma-ray was irradiated 30 minutes thereafter. Carcinoma was extracted and treated with trypsin to prepare a cell suspension. The survival rate was determined by the colony forming method. A physiological saline solution was administered to the control. The results are shown in Table 2.

TABLE 2

| Sample | Hypoxic cell survival rate (%) |
| --- | --- |
| No radiation, physiological saline administered | 36.21 |
| Radiation, physiological saline administered | 0.81 |
| RS-SR racemate | 0.08 |
| SS isomer | 0.07 |
| RR isomer | 0.07 |
| RS or SR isomer (rotation(+)) | 0.08 |
| RS or SR isomer (rotation(−)) | 0.08 |

As can be seen in Table 2, the optical isomers of the present invention have the same degree of excellent hypoxic cell radiosensitization effects as the racemate, indication their effectiveness for the radiation therapy of cancer.

Test Example 3 (Dissolution test)

Solubilities of SS, RR, SR, and RS isomers and SR-RS racemate in water and physiological saline were determined. The results are shown in Table 3.

TABLE 3

|  | Solubility in water (g/ml) | Solubility in physiological saline (g/ml) |
| --- | --- | --- |
| SS isomer | 0.85 | 0.82 |
| RR isomer | 0.74 | 0.87 |
| RS or SR isomer (rotation(+)) | N.A. | 0.07 |
| RS or SR isomer (rotation(−)) | N.A. | 0.06 |
| SR-RS racemate | 0.04 | 0.04 |

As can be seen from the results shown in Table 3, the solubilities of SS, RR, SR, and RS isomers are remarkably larger than that of SR-RS racemate. This indicates a great advantage of the compounds of the present invention in that the amount of aqueous carriers can be greatly reduced in injection, a conceivable ideal form for a hypoxic cell radiosensitizer of which a dose must be a large amount.

Test Example 4

Determination of octanol-phosphate partition coefficient

The partition coefficient in the octanol-phosphate buffer solution system, which is indicative of the degree of orientation toward nerve tissues, was determined. Amounts of 1.4 times and 0.7 times the solubility in octanol of each sample were precisely weighed. To the weighed samples 10 ml of 0.2 mol phosphate buffer (pH 7.4), defined in the Pharmacopoeia of Japan, and 10 ml of octanol were added. The mixtures were shaken for 24 hours at 20° C. under light shielding. Octanol and phosphate layers were partitioned to determine the absorbance of each layer. The partition coefficients at 1.4 and 0.7 times the solubility in octanol were determined from the ratio of the absorbances. The partition coefficients obtained were averaged to determine the partition coefficient of each sample. The results are shown in Table 4.

TABLE 4

|  | 1.4 times | 0.7 time | partition coefficient |
|---|---|---|---|
| SS isomer | 0.026 | 0.031 | 0.028 |
| RR isomer | 0.024 | 0.026 | 0.025 |
| RS or SR isomer (rotation(+)) | 0.053 | 0.059 | 0.056 |
| RS or SR isomer (rotation(−)) | 0.048 | 0.058 | 0.053 |
| SR-RS racemate | 0.037 | 0.057 | 0.047 |
| Misonidazole | 0.378 | 0.401 | 0.390 |

As clear from the results shown in Table 4, among the optically active isomers SS isomer and RR isomer are less partitioned toward the octanol layer, and are thus less exhibitive of nerve toxicity.

Test Example 5 (Acute toxicity test)

Test compounds, dissolved in physiological saline or a physiological saline solution containing 10% DMSO, were intravenously or intraperitoneally injected to ICR male mice, aged 5 weeks. The mice were observed for 14 days after the injection to determine the median lethal dose ($LD_{50/14}$). The results are shown in Table 5.

TABLE 5

| Compound of the present invention | $LD_{50/14}$ (mg/kg) |
|---|---|
| Compound (1) | 6,000 |
| Compound (2) | 6,000 |
| Compound (3) | 5,900 |
| Compound (4) | 5,900 |

Test Example 6 (Acute toxicity test)

The acute toxicity was determined using groups of male ICR mice, aged 5 weeks, each group consisting of five mice. Test compounds were dissolved in physiological saline and administered by injection through caudal vein. The death-survival determination was made 14 days after the administration. The results in terms of dead animals/tested animals are in Table 6.

TABLE 6

|  | Dose (mg/kg) | | |
|---|---|---|---|
|  | 3000 | 6000 | 9000 |
| SS isomer | 0/5 | 1/5 | 5/5 |
| RR isomer | 0/5 | 3/5 | N.A. |
| SR isomer | 0/5 | 3/5 | N.A. |
| RS isomer | 0/5 | 3/5 | N.A. |
| SR-RS racemate | 0/5 | 3/5 | N.A. |

As clear from the results shown in Table 6, SS isomer exhibited better safety than other optically active isomers.

Test Example 7 (Acute toxicity test)

Exhibition of toxicity of SR-RS racemate and SS isomer were tested by intravenous injection (500 mg) to beagle dogs. The results are shown in Table 7.

TABLE 7

|  | Exhibition of toxicity |
|---|---|
| SR-RS racemate | The dog vomited 60, 80, 90 minutes after the injection |
| SS isomer | The dog exhibited no change in 24 hours after the injection |

As clear from the results shown in Table 7, the SS isomer exhibited remarkably suppressed nerve toxicity as compared with the SR-RS racemate.

Industrial Applicability

High purity 2-nitroimidazole derivatives can be prepared at a high yield from inexpensive diester of tartaric acid by the present invention. The 2-nitroimidazoles obtained exhibit excellent radiosensitivity and high safety. The compounds are thus suitable as a drug to be used along with radiotherapy of various cancers.

We claim:

1. A 2-nitroimidazole derivative represented by any one of the following formulas (1) or (2),

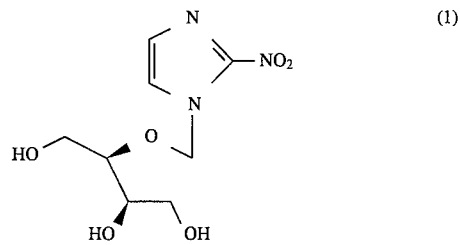

(1)

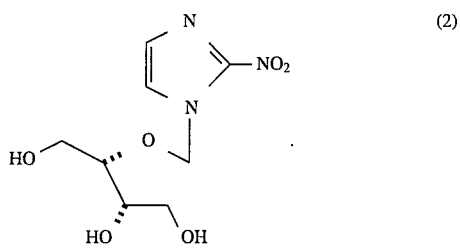

(2)

2. The compound of claim 1 which is (1) 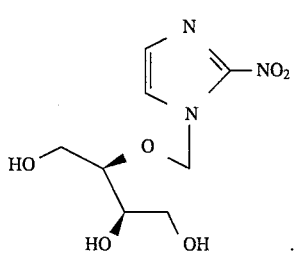

3. The compound of claim 1 which is (2) 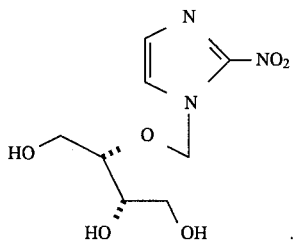

4. A radiosensitizer composition comprising a radiosensitizer effective mount of the compound of claim 1, in non-racemic form and in substantially optically pure form and a carrier.

5. The composition of claim 4 wherein the compound of claim 1 is a compound having formula 1.

6. The composition of claim 4 wherein the compound of claim 1 is a compound having formula 2.

7. The composition of claim 5, wherein the compound of formula 1 has a solubility in water of about 0.74 g/ml.

8. The composition of claim 6, wherein the compound of formula 2 has a solubility in water of about 0.85g/ml.

9. The compound of claim 1 of formula (2) having an optical purity of 99.5%.

* * * * *